(12) United States Patent
Brown

(10) Patent No.: US 11,935,162 B2
(45) Date of Patent: Mar. 19, 2024

(54) PROTOCOL-DEPENDENT 2-D PRE-SCAN PROJECTION IMAGE BASED ON 3-D PRE-SCAN VOLUMETRIC IMAGE DATA

(71) Applicant: KONINKLIJKE PHILIPS N.V., Eindhoven (NL)

(72) Inventor: Kevin Martin Brown, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 201 days.

(21) Appl. No.: 17/610,845

(22) PCT Filed: May 13, 2020

(86) PCT No.: PCT/EP2020/063257
§ 371 (c)(1),
(2) Date: Nov. 12, 2021

(87) PCT Pub. No.: WO2020/229504
PCT Pub. Date: Nov. 19, 2020

(65) Prior Publication Data
US 2022/0207795 A1     Jun. 30, 2022

Related U.S. Application Data

(60) Provisional application No. 62/847,384, filed on May 14, 2019.

(51) Int. Cl.
*A61B 6/00*     (2006.01)
*G06T 11/00*    (2006.01)

(52) U.S. Cl.
CPC ............ *G06T 11/008* (2013.01); *A61B 6/463* (2013.01); *A61B 6/488* (2013.01); *A61B 6/5205* (2013.01)

(58) Field of Classification Search
CPC ....... G06T 11/008; A61B 6/463; A61B 6/488; A61B 6/5205; A61B 6/032; A61B 6/505;
(Continued)

(56) References Cited

U.S. PATENT DOCUMENTS 9,730,759 B2 *   8/2017  Schirra ............... A61B 6/5217
10,045,754 B2    8/2018  Klinder
(Continued)

FOREIGN PATENT DOCUMENTS

CN          107909622 A       4/2018

OTHER PUBLICATIONS

PCT International Search Report, International application No. PCT/EP2020/063257, dated Jul. 21, 2020.
(Continued)

*Primary Examiner* — Kiho Kim
(74) *Attorney, Agent, or Firm* — Larry Liberchuk

(57) ABSTRACT

An imaging system (302) includes an X-ray radiation source (312) configured to emit radiation that traverses an examination region, a detector array (314) configured to detect radiation that traverses an examination region and generate a signal indicative thereof, wherein the detected radiation is for a 3-D pre-scan, and a reconstructor (316) configured to reconstruct the signal to generate a 2-D pre-scan projection image. The imaging system further includes a console (318) wherein a processor thereof is configured to execute 3-D volume planning instructions (328) in memory to display the 2-D pre-scan projection image (402, 602, 802, 1002) and a scan plan or bounding box (404, 604, 804, 1004) for planning a 3-D volume scan of a region/tissue of interest based on a selected protocol for a 3-D volume scan of a region/tissue of interest being planned and receive an input
(Continued)

confirming or adjusting the scan plan box to create a 3-D volume scan plan for the 3-D volume scan of the region/tissue of interest.

17 Claims, 7 Drawing Sheets

(58) Field of Classification Search
CPC ....... A61B 6/466; A61B 6/469; A61B 6/5223; A61B 6/545; G06N 20/00
See application file for complete search history.

(56) References Cited

U.S. PATENT DOCUMENTS

| | | | |
|---|---|---|---|
| 2007/0183649 A1* | 8/2007 | Kiefer | G06T 15/005 382/154 |
| 2007/0276220 A1 | 11/2007 | Harvey | |
| 2008/0234571 A1 | 9/2008 | Hay | |
| 2012/0163687 A1 | 6/2012 | Plakas | |
| 2014/0270434 A1 | 9/2014 | Gulaka | |
| 2015/0043774 A1 | 2/2015 | Harder | |
| 2016/0287201 A1* | 10/2016 | Bergtholdt | A61B 6/4435 |
| 2018/0184997 A1 | 7/2018 | Tsukagoshi | |
| 2018/0360316 A1 | 12/2018 | Kuo | |

OTHER PUBLICATIONS

Yin Z. et al., "Acquisition, Preprocessing, and Reconstruction of Ultralow Dose Volumetric CT Scout Organ-Based Scan Planning", Medical Physics, vol. 42, No. 5, pp. 2730-2739, May 2015.

* cited by examiner

PROTOCOL-DEPENDENT 2-D PRE-SCAN PROJECTION IMAGE BASED ON 3-D PRE-SCAN VOLUMETRIC IMAGE DATA

FIELD OF THE INVENTION

The following generally relates to imaging and more particularly to a protocol-dependent two-dimensional (2-D) pre-scan projection image that is based on three-dimensional (3-D) pre-scan volumetric image data and is described with particular application to computed tomography (CT).

BACKGROUND OF THE INVENTION

A computed tomography (CT) scanner includes an X-ray tube that rotates around an examination region and emits X-ray radiation that traverses the examination region. A detector array detects X-ray radiation that traverses the examination region and an object or subject therein (which attenuates the X-ray radiation) and is incident thereon. The detector array generates projection data indicative of the incident X-ray radiation. A reconstructor reconstructs the projection data to generate three-dimensional (3-D) volumetric image data indicative of the examination region and the object or subject therein.

Prior to performing the volume scan, a pre-scan is performed to generate a 2-D pre-scan projection image to plan the volume scan. Historically, the pre-scan (also referred to as a scout, a pilot or a surview) is performed with the X-ray tube statically positioned at a given angle and moving the object or subject along a longitudinal scan axis (Z-axis) through the examination region while the X-ray tube emits X-ray radiation. The reconstructor reconstructs the acquired data to generate the 2-D pre-scan projection image, which mimics an X-ray image and shows the interior of the object or subject.

The extent of the object or subject scanned during the pre-scan is such that a region/tissue of interest for the volume scan is visible in the 2-D pre-scan projection image. For example, a pre-scan for a lung scan may cover from the shoulders to the pelvis. To plan the volume scan, the user identifies the Z-axis extent on the 2-D pre-scan projection image for the region/tissue of interest. This has been through a scan plan or bounding box, which defines start and end scan locations for the region/tissue of interest to be scanned. FIG. 1 shows a prior art 2-D pre-scan projection image 102 with an example scan plan or bounding box 104 superimposed thereover.

U.S. Pat. No. 10,045,754 B2, which is incorporated in its entirety herein by reference, discusses a low dose 3-D pre-scan, which is similar to a 2-D pre-scan except that X-ray tube rotates during the scan to acquire tomographic data, which is reconstructed to produce 3-D pre-scan volumetric image data. This 3-D pre-scan volumetric image data has poorer contrast resolution than diagnostic 3-D volumetric image data from a diagnostic scan and is not used for diagnostic purposes. For planning, the 3-D pre-scan volumetric image data is used to generate a 2-D pre-scan projection image, e.g., by summing the 3-D volume along ray paths.

The 2-D pre-scan projection image generated from the data acquired during the 3-D pre-scan is similar to the 2-D pre-scan projection image generated from the data acquired during the 2-D pre-scan and can be similarly employed to plan the volume scan of the region/tissue of interest. For example, the user can use a scan plan or bounding box to define start and end scan locations for the region/tissue of interest to be scanned. FIG. 2 shows an example of such a 2-D pre-scan projection image 202 along with an example scan plan or bounding box 204.

Unfortunately, the 2-D pre-scan projection image in either case (i.e. from the 2-D pre-scan acquisition, e.g., as shown in FIG. 1, and from the 3-D pre-scan acquisition, e.g., as shown in FIG. 2) reveals only limited 2-D information about the tissue of interest to be scanned. For example, in FIGS. 1 and 2 there is no clear delineation between the lungs and the diaphragm at the lung/diaphragm interface. As such, the scan plan or bounding box is often extended by some margin in the Z-axis direction to ensure the region is scanned, e.g., to avoid having to re-scan the object or subject due to not scanning the entire region of interest.

SUMMARY OF THE INVENTION

Aspects described herein address the above-referenced problems and/or others.

For instance, the following describes an approach that in one instance displays 2-D pre-scan projections images using different rendering algorithms to visually enhance a region/tissue of interest in a displayed 2-D pre-scan projection image, where the region/tissue of interest is determined from the scan protocol.

In one aspect, an imaging system includes an X-ray radiation source configured to emit radiation that traverses an examination region, a detector array configured to detect radiation that traverses an examination region and generate a signal indicative thereof, wherein the detected radiation is for a 3-D pre-scan, and a reconstructor configured to reconstruct the signal to generate a 2-D pre-scan projection image. The imaging system further includes a console with a processor and a memory, wherein the processor is configured to execute 3-D volume planning instructions in the memory, which causes the processor to: display the 2-D pre-scan projection image and a scan plan or bounding box for planning a 3-D volume scan of a region/tissue of interest based on a selected protocol for a 3-D volume scan of a region/tissue of interest being planned, and receive an input confirming or adjusting the scan plan or bounding box to create a 3-D volume scan plan for the 3-D volume scan of the region/tissue of interest. The 3-D volume scan of the region/tissue of interest is performed based on the 3-D volume scan plan.

In another aspect, a method includes obtaining projection data from a 3-D pre-scan. The method further includes reconstructing the projection data to create a 2-D pre-scan projection image. The method further includes displaying the 2-D pre-scan projection image and a scan plan or bounding box for planning a 3-D volume scan of a region/tissue of interest based on a selected protocol for a 3-D volume scan of a region/tissue of interest being planned. The method further includes receiving an input confirming or adjusting the scan plan or bounding box to create a 3-D volume scan plan for the 3-D volume scan of the region/tissue of interest.

In another aspect, a computer-readable storage medium stores instructions that when executed by a processor of a computer cause the processor to: obtain projection data from a 3-D pre-scan, reconstruct the projection data to create a 2-D pre-scan projection image, display the 2-D pre-scan projection image and a scan plan or bounding box for planning a 3-D volume scan of a region/tissue of interest based on a selected protocol for a 3-D volume scan of a region/tissue of interest being planned, and receive an input confirming or adjusting the scan plan or bounding box to create a 3-D volume scan plan for the 3-D volume scan of the region/tissue of interest.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the embodiments and are not to be construed as limiting the invention.

DETAILED DESCRIPTION OF EMBODIMENTS

The following describes an approach for generating a 2-D pre-scan image from data acquired with a 3-D pre-scan and based on a scan protocol for a region/tissue of interest for a volume scan of the region/tissue of interest being planned with the 2-D pre-scan image. In one instance, this allows for displaying differently rendered 2-D pre-scan images to visually enhance the region/tissue of interest in the 2-D pre-scan image.

Figure 2:
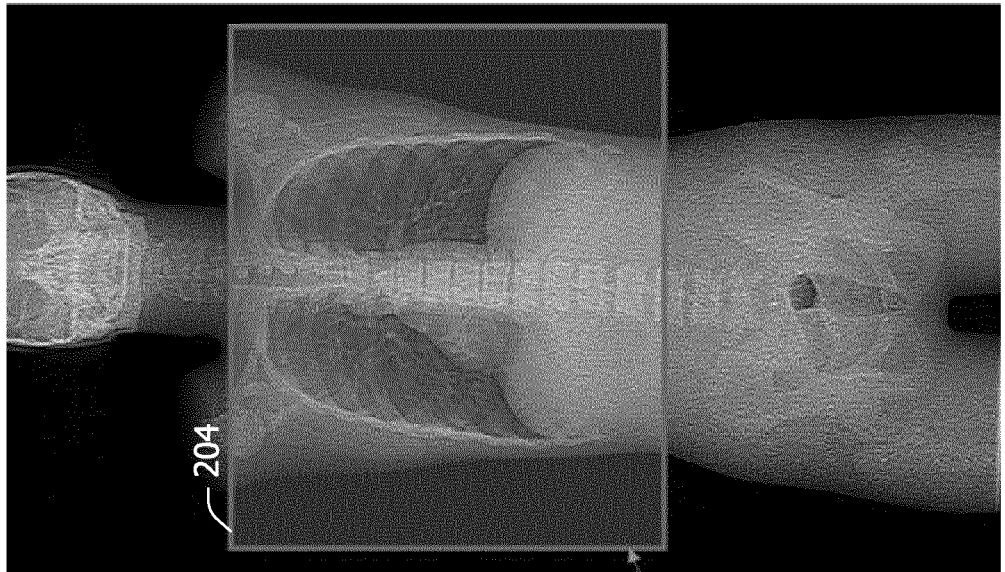
FIG. 2 shows a prior art 2-D pre-scan projection image created from data acquired during a 3-D pre-scan and a scan plan or bounding box.
Figure 1:
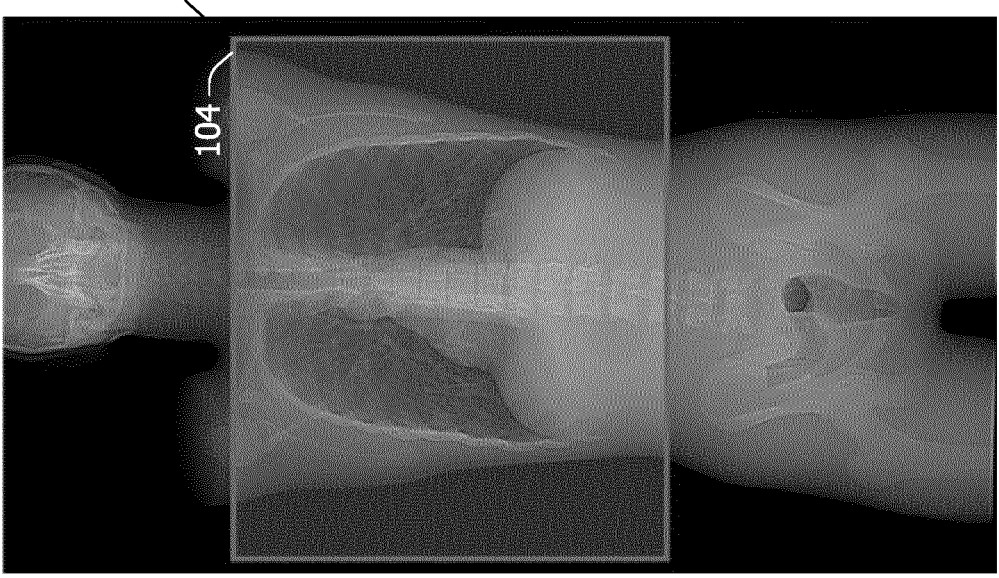
FIG. 1 shows a prior art 2-D pre-scan projection image created from data acquired during a 2-D pre-scan and a scan plan or bounding box.
Figure 3:
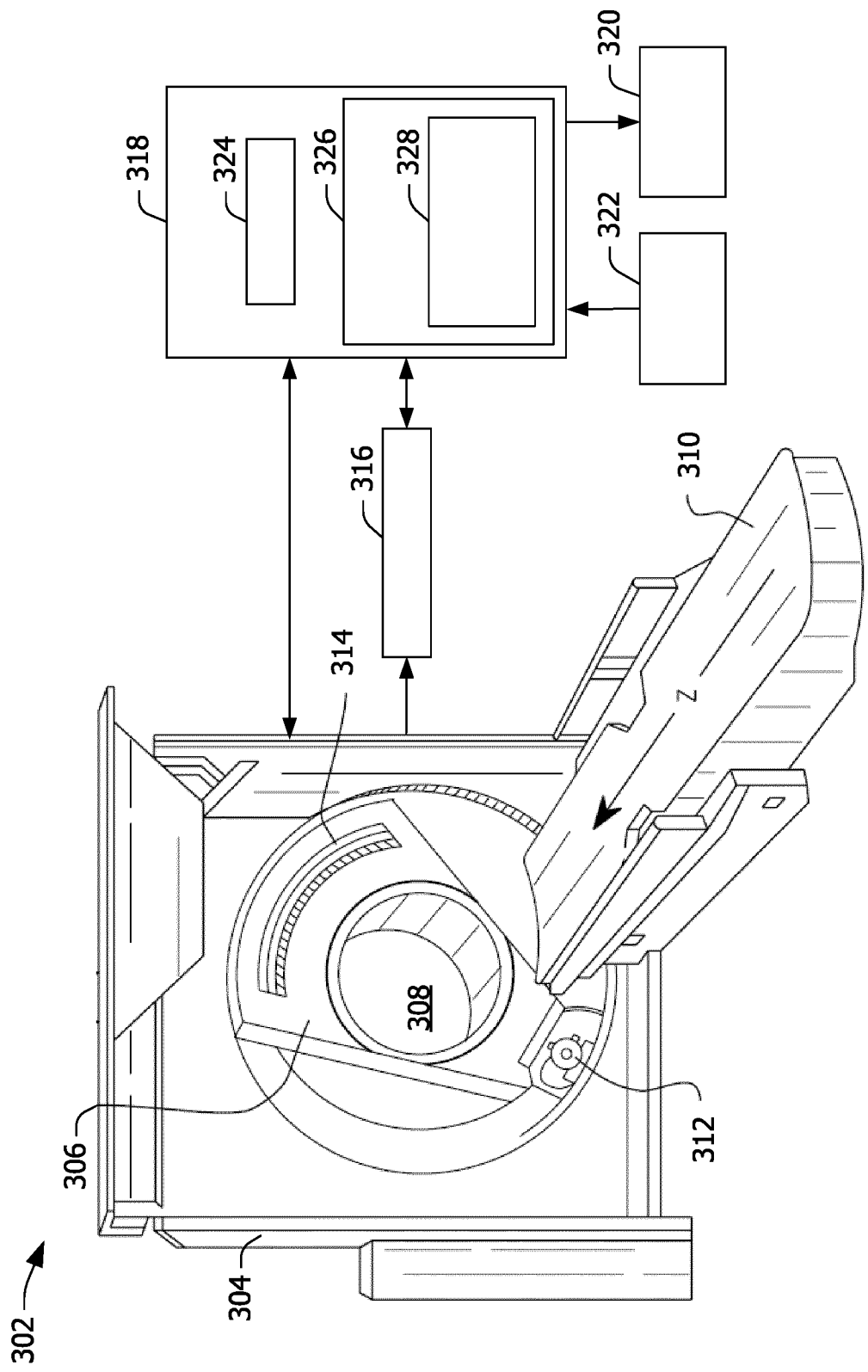
FIG. 3 diagrammatically illustrates an example imaging system including 3-D volume planning instructions, in accordance with an embodiment(s) herein.

FIG. 3 illustrates an imaging system 302 such as a computed tomography (CT) scanner. The illustrated imaging system 302 includes a stationary gantry 304 and a rotating gantry 306, which is rotatably supported by the stationary gantry 304. The rotating gantry 306 rotates around an examination region 308 about a longitudinal axis ("Z"). A subject support 310, such as a couch, supports a subject or object in the examination region 308 and guides the subject or object for loading, scanning, and/or unloading of the subject or object.

An X-ray radiation source 312, such as an X-ray tube, is supported by the rotating gantry 306 and rotates with the rotating gantry 306 about the examination region 308 and emits X-ray radiation that traverses the examination region 308. An X-ray radiation sensitive detector array 314 is located opposite the X-ray radiation source 312 across the examination region 308. The X-ray radiation sensitive detector array 314 detects X-ray radiation traversing the examination region 308 (and an object or subject therein) and generates a signal (i.e. projection data, or line integrals) indicative thereof.

A reconstructor 316 is configured to reconstruct the signal from the X-ray radiation sensitive detector array 314 to generate image data. For example, in one instance the reconstructor 316 is configured to reconstruct a 2-D pre-scan image with data acquired from a 2-D pre-scan and/or a 3-D pre-scan. For the 3-D pre-scan data, this may include reconstructing 3-D pre-scan volumetric image data and then generating the 2-D pre-scan image therefrom. Additionally, or alternatively, the reconstructor 316 is configured to reconstruct diagnostic 3-D volumetric image data with data acquired from a diagnostic 3-D volume scan planned with the 2-D pre-scan image.

In one instance, the reconstructor 316 is implemented with hardware such as a central processing unit (CPU), a microprocessor (μCPU), a graphics processing unit (GPU), an application specific integrated circuit (ASIC), etc. configured to execute computer executable instructions stored, embedded, encoded, etc. on computer readable storage medium and/or non-transitory memory. The reconstructor 316 can be part of the system 302 (as shown) and/or remote therefrom, e.g., in a remote computing system, distributed across other computing systems, part of "cloud" based resources, etc.

An operator console 318 includes a human readable output device(s) 320 such as a display monitor, a filmer, etc., and an input device(s) 322 such as a keyboard, mouse, etc. The operator console 318 further includes a processor 324 (e.g., a CPU, a μCPU, etc.) and computer readable storage medium ("memory") 326 (which excludes transitory medium) such as physical memory like a memory storage device, etc. The computer readable storage medium 326 includes computer readable instruction. The processor 324 is configured to execute at least the computer readable instructions.

In one instance, the computer readable instructions include at least 3-D data acquisition instructions and reconstruction instructions. Examples of suitable data acquisitions include 2-D pre-scans and/or 3-D pre-scans, and diagnostic 3-D volume scans. Examples of suitable reconstructions include a 2-D pre-scan projection image from the data acquired with the 2-D pre-scan and/or a 2-D pre-scan projection image from the data acquired with the 3-D pre-scans, and a diagnostic 3-D volumetric image data from data acquired from a diagnostic 3-D volume scan.

The computer readable instructions also include 3-D volume planning instructions 328. As described in greater detail below, the 3-D volume planning instructions 328 include instructions for creating and displaying a 2-D pre-scan projection image generated from data acquired with a 3-D pre-scan and based on a scan protocol for a region/tissue of interest for a 3-D volume scan of the region/tissue of interest being planned with the 2-D pre-scan image. In one instance, the scan protocol is obtained from an order prescribed by a clinician (e.g., a referring physician, a radiologist, etc.) and entered/selected by a user setting up the imaging system 302 to scan the subject via the input device(s) 322 of the console 318 and/or otherwise.

Non-limiting examples of 2-D pre-scan projection image generated from data acquired with a 3-D pre-scan and based on a scan protocol for a region/tissue of interest for a 3-D volume scan of the region/tissue of interest being planned with the 2-D pre-scan image are described next.

In one example, the scan protocol is for a scan of the ribs, and the executing instructions 328 selects a rendering algorithm for the ribs. In this example, the selected rendering algorithm is a Maximum Intensity Projection (MIP) rendering algorithm since the tissue of interest is bone, which greatly attenuates X-rays, which results in voxels with values representing bone, or materials represented through high intensities. In general, a MIP is a rendering technique for projecting the voxel with the maximum intensity along a ray from a given viewpoint to a plane of projection.

In one instance, the executing instructions 328 determine, from a predetermined mapping, look up table (LUT), etc., a rendering algorithm for the scan protocol for the ribs. That is, the mapping, etc. may include a data structure that maps each type of scan protocol to a rendering algorithm and that is stored in the memory 326 and/or other storage device. The mapping, etc. can be pre-determined based on empirical and/or theoretical data. In another instance, the user specifies the rendering algorithm of interest. In yet another example, the instructions 328 include an artificial intelligence (e.g., machine learning) that learns the mapping, etc. from user selections/preferences of individual clinicians and/or healthcare facilities.

Figure 4:
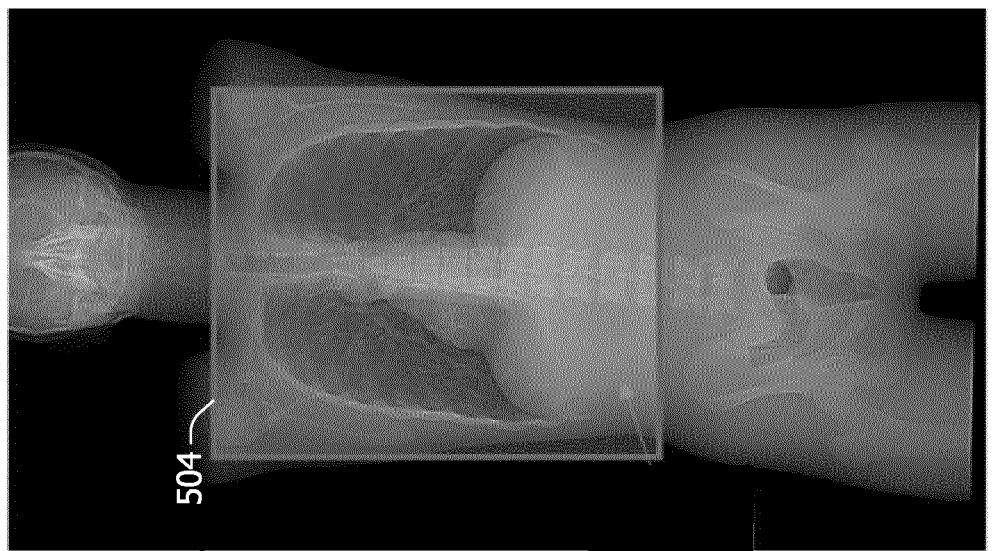
FIG. 4 shows an anterior rib MIP 2-D pre-scan projection image created from data acquired during a 3-D pre-scan and a scan plan or bounding box, in accordance with an embodiment(s) herein.
Figure 5:
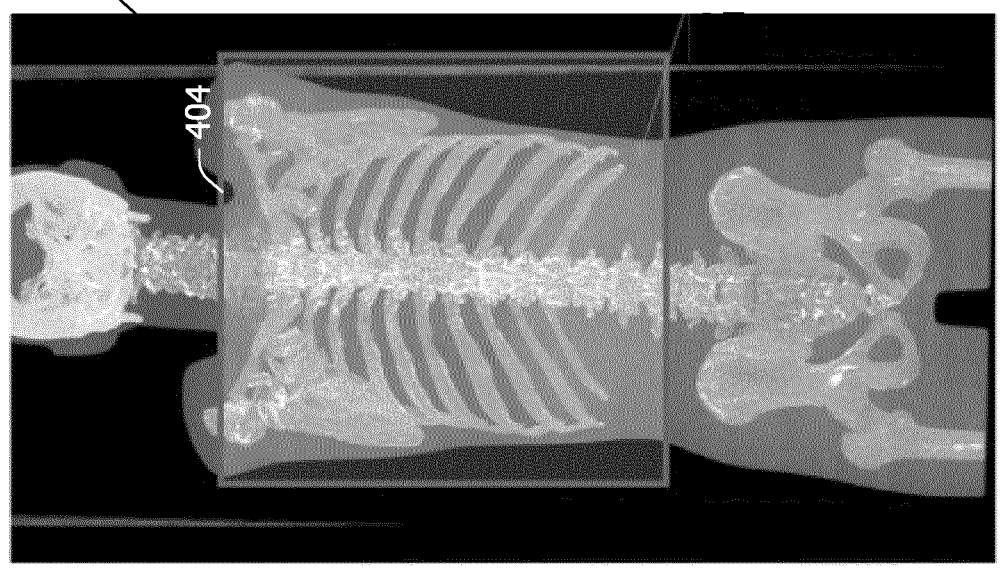
FIG. 5 shows a prior art anterior rib 2-D pre-scan projection image created from data acquired during a 2-D pre-scan and a scan plan or bounding box.

FIG. 4 shows a 2-D pre-scan projection image 402 of an anterior view of a subject generated from data acquired during a 3-D pre-scan based on a scan protocol for the ribs along with a scan plan or bounding box 404. For comparison, FIG. 5 shows a prior art 2-D pre-scan projection image 502 of an anterior view of a subject generated from data acquired during a 2-D or 3-D pre-scan 3-D, which is not based on the scan protocol, and a scan plan or bounding box 504. From FIGS. 4 and 5, the ribs are visually enhanced (i.e. brighter) in the 2-D pre-scan projection image of FIG. 4 relative to the 2-D pre-scan projection image of FIG. 5. In one instance, this allows the operator to more easily confirm sufficient coverage with and/or adjust the scan plan or bounding box 404 for sufficient coverage of the ribs of interest.

Figure 7:
FIG. 7 shows a prior art lateral spine 2-D pre-scan projection image created from data acquired during a 2-D pre-scan and a scan plan or bounding box.
Figure 6:
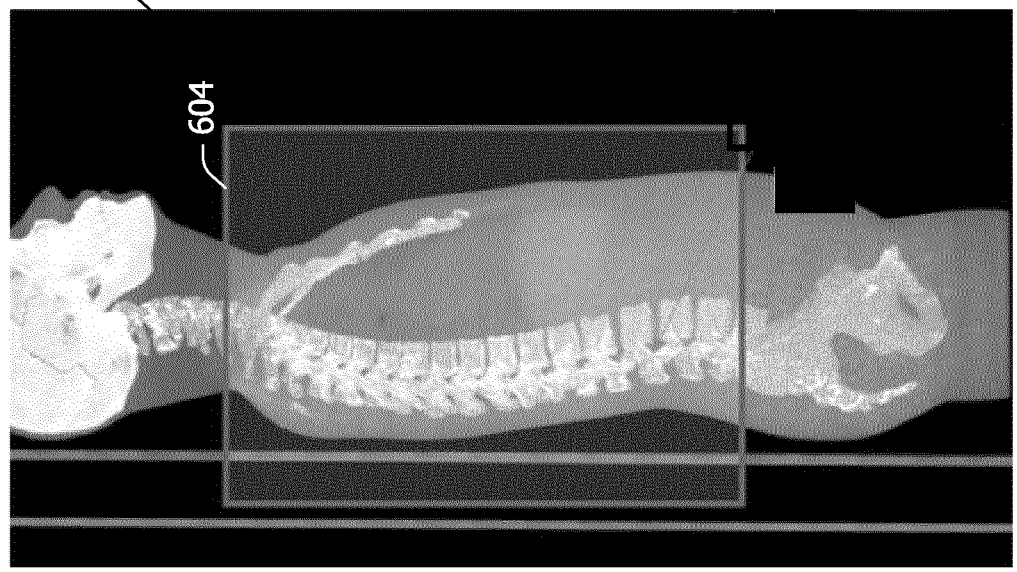
FIG. 6 shows a lateral spine MIP 2-D pre-scan projection image created from data acquired during a 3-D pre-scan and a scan plan or bounding box, in accordance with an embodiment(s) herein.

In another example, the scan protocol is for a scan of the spine. In this example, the executing instructions 328 again selects a MW rendering algorithm since the tissue of interest is bone. FIG. 6 shows a 2-D pre-scan projection image 602 of a lateral view of a subject generated from data acquired during a 3-D pre-scan based on a scan protocol for the spine along with a scan plan or bounding box 604. For comparison, FIG. 7 shows a prior art 2-D pre-scan projection image 702 of a lateral view of a subject generated from data acquired during a 2-D or 3-D pre-scan, which is not based on the scan protocol, and a scan plan or bounding box 704. From FIGS. 6 and 7, the spine is visually enhanced (i.e. brighter) in the 2-D pre-scan projection image of FIG. 6 relative to the 2-D pre-scan projection image of FIG. 7. Likewise, this allows the operator to more easily confirm sufficient coverage with and/or adjust the scan plan or bounding box 604 for sufficient coverage of the vertebrae of interest.

Figure 9:
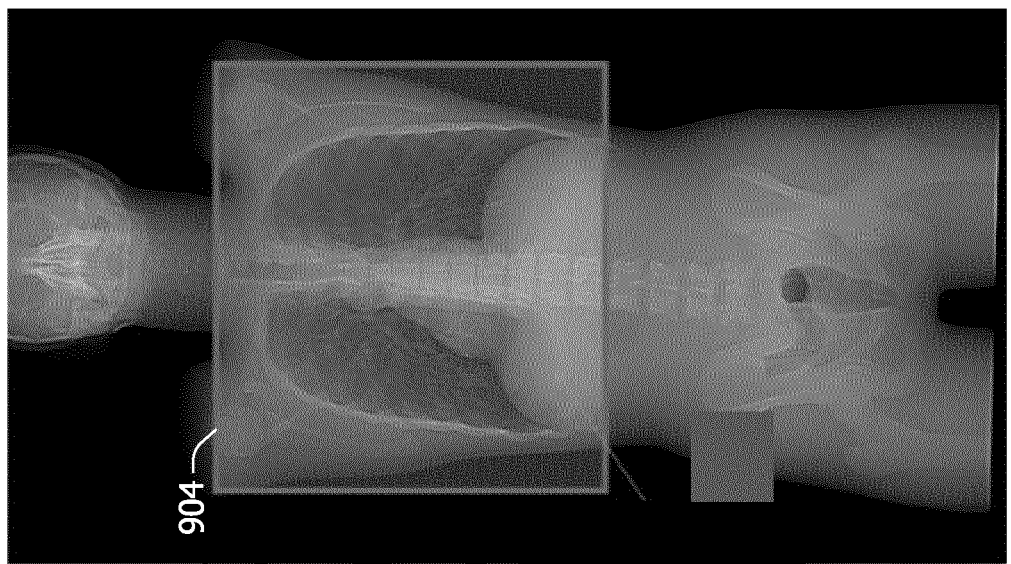
FIG. 9 shows a prior art anterior lung 2-D pre-scan projection image created from data acquired during a 2-D pre-scan and a scan plan or bounding box.
Figure 8:
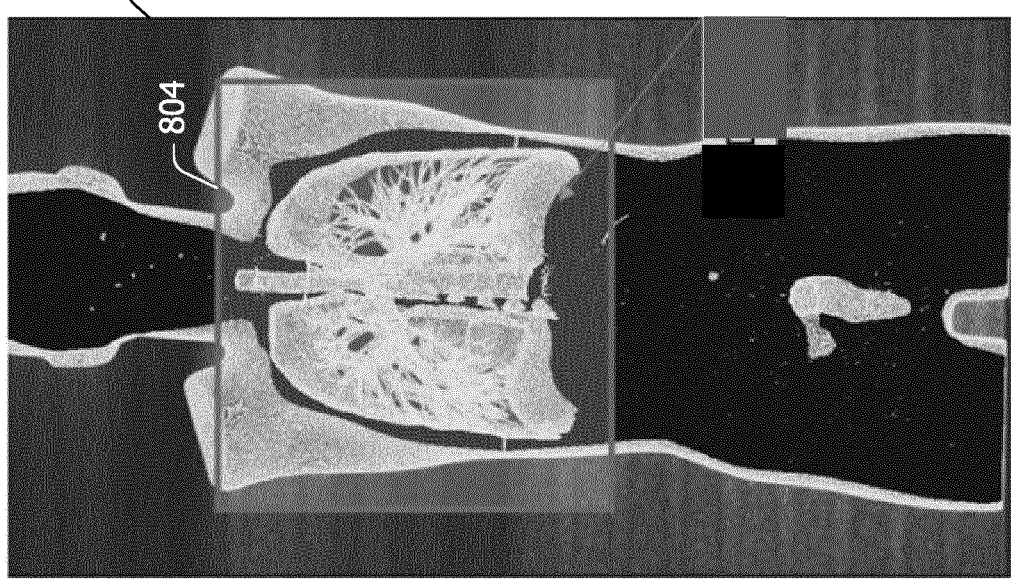
FIG. 8 shows an anterior lung MIP 2-D pre-scan projection image created from data acquired during a 3-D pre-scan and a scan plan or bounding box, in accordance with an embodiment(s) herein.

In another example, the scan protocol is for a scan of the lungs. In this example, the executing instructions 328 selects an air/soft tissue (ST Edge) interface rendering algorithm since the lungs are soft tissue filled with and surrounded by air. FIG. 8 shows a 2-D pre-scan projection image 802 of an anterior view of a subject generated from data acquired during a 3-D pre-scan based on a scan protocol for the lungs along with a scan plan or bounding box 804. For comparison, FIG. 9 shows a prior art 2-D pre-scan projection image 702 of an anterior view of a subject generated from data acquired during a 2-D or 3-D pre-scan 3-D, which is not based on the scan protocol, and a scan plan or bounding box 904. From FIGS. 8 and 9, the lungs are visually enhanced (i.e. brighter) in the 2-D pre-scan projection image of FIG. 8 relative to the 2-D pre-scan projection image of FIG. 9. This allows the operator to more easily confirm sufficient coverage with and/or adjust the scan plan or bounding box 804 for sufficient coverage of the lungs.

Figure 11:
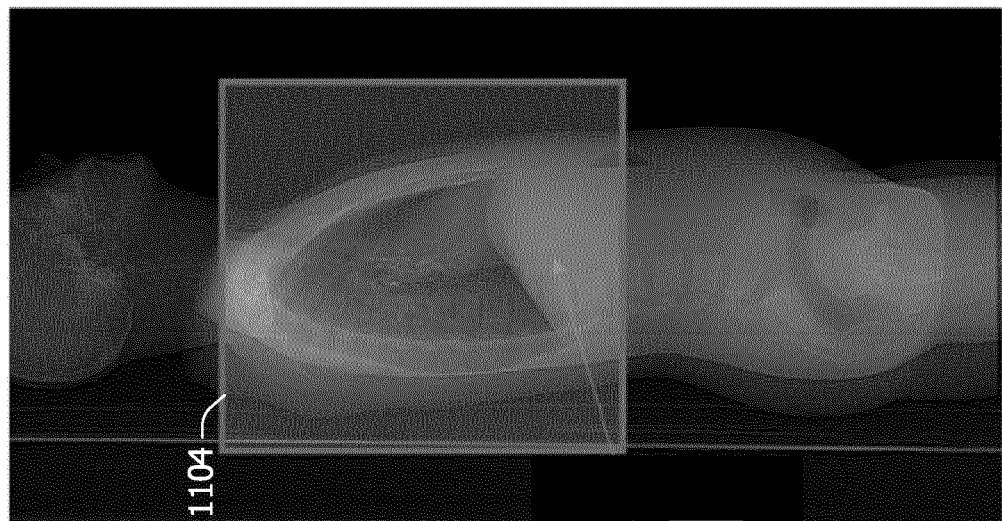
FIG. 11 shows a prior art lateral lung 2-D pre-scan projection image created from data acquired during a 2-D pre-scan and a scan plan or bounding box.
Figure 10:
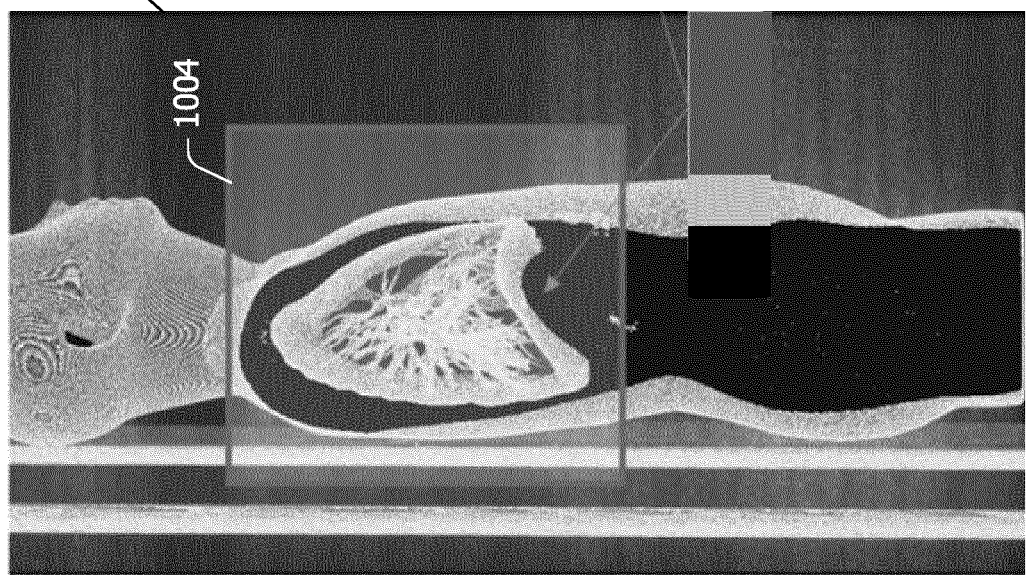
FIG. 10 shows a lateral lung MIP 2-D pre-scan projection image created from data acquired during a 3-D pre-scan and a scan plan or bounding box, in accordance with an embodiment(s) herein.

In another example, the scan protocol is again for a scan of the lungs. The executing instructions 328 likewise selects an air/soft tissue (ST Edge) interface rendering algorithm since the lungs are soft tissue filled with and surrounded by air. FIG. 10 shows a 2-D pre-scan projection image 1002 of a lateral view of a subject generated from data acquired during a pre-scan 3-D based on a scan protocol for the lungs along with a scan plan box 1004. For comparison, FIG. 11 shows a prior art 2-D pre-scan projection image 1102 of a lateral view of a subject generated from data acquired during a 2-D or 3-D pre-scan 3-D, which is not based on the scan protocol, and a scan plan box 1104. From FIGS. 10 and 11, the lungs are visually enhanced (i.e. brighter) in the 2-D pre-scan projection image of FIG. 10 relative to the 2-D pre-scan projection image of FIG. 11. Similarly, this allows the operator to more easily confirm sufficient coverage with and/or adjust the scan plan or bounding box 1004 for sufficient coverage of the lungs.

Returning to FIG. 3, in one instance, the console 318, during volume scan planning, only displays the visually enhanced 2-D pre-scan projection image (e.g., 2-D pre-scan projection images 402, 602, 802 or 1002). In another instance, the console 318, during volume scan planning, displays both the visually enhanced 2-D pre-scan projection image (e.g., 2-D pre-scan projection images 402, 602, 802 or 1002) and the non-visually enhanced 2-D pre-scan projection image (e.g., 2-D pre-scan projection images 502, 702, 902 or 1102). In another instance, a user can toggle between visually enhanced 2-D pre-scan projection image and non-visually enhanced 2-D pre-scan projection image. The images displayed can be determined automatically by the instructions 328 and/or defined by the operator, via operator preferences or otherwise, for each different type of scan and/or examination. The operator can confirm and/or adjust (e.g., increase or decrease the Z-axis extent) and then confirm scan plan or bounding box.

Suitable rendering algorithms include algorithms for projecting 3-D data into a 2-D plane. Non-limiting examples includes, but are not limited to, MIP, ST Edge, Minimum Intensity Projection (MinIP) which is the negative of MIP and projects the voxel with the lowest intensity, Multiplanar Reconstruction (MPR) which reformats the volumetric to generate a 2-D pre-scan projection image in a axial, sagittal, coronal, and/or oblique plane, curved MPR (cMPR) which effectively straightens a curved structure (e.g., the spine, vessels, etc.) so that the entire length of a section or the entire curved structure is concurrently visualized in the same plane, and/or other volume rendering techniques.

In one instance, the approach described herein allows for a more accurate volume scan plan in that the boundaries of the scan plan or bounding box can more accurately fit to the region/tissue of interest relative to volume scan plan planned using the prior art 2-D pre-scan projection image, which does not visually enhance the region/tissue of interest. In one instance, this may reduce over-all patient dose relative to a configuration in which the prior art 2-D pre-scan projection image is created by adding a margin to ensure the region/tissue of interest is covered in the pre-scan by mitigating the margin.

In addition, or alternative, to planning a volumetric scan, the 2-D pre-scan projection images described herein, which are generated based on data acquired during a 3-D pre-scan and a selected scan protocol for a region/tissue of interest, can also be used in trauma or other instances, e.g., to identify a fracture of a bone directly from the 2-D pre-scan projection image, which, in one instance, saves time and/or reduces patient dose.

Where the imaging system 302 is configured for spectral (multi-energy) imaging, the visually enhanced 2-D pre-scan projection image may leverage spectral properties. For example, the visually enhanced 2-D pre-scan projection image may be a contrast only or a virtual non-contrast visually enhanced 2-D pre-scan projection image, e.g., where the region/tissue of interest includes vessels, etc. In this instance, the predetermined mapping, etc. (or other mapping, etc.) includes a type of spectral image data for each scan protocol, the user will select the type of spectral image data of interest, and/or the artificial intelligence algorithm will also learn the type of spectral image data from user selections for individual clinicians and/or healthcare facilities.

Generally, a spectral configuration will include an X-ray tube configured to emit broadband (polychromatic) radiation for a single selected peak emission voltage of interest and the radiation sensitive detector array will include an energy-resolving detector such as a multi-layer scintillator/photosensor detector and/or a photon counting (direct conversion) detector, or an X-ray tube configured to switch between at least two different emission voltages during a scan and/or two or more X-ray tubes angular offset on the rotating gantry with each configured to emit radiation with a different mean energy spectrum and the radiation sensitive detector array will a non-energy resolving detector and/or an energy-resolving detector.

Figure 12:
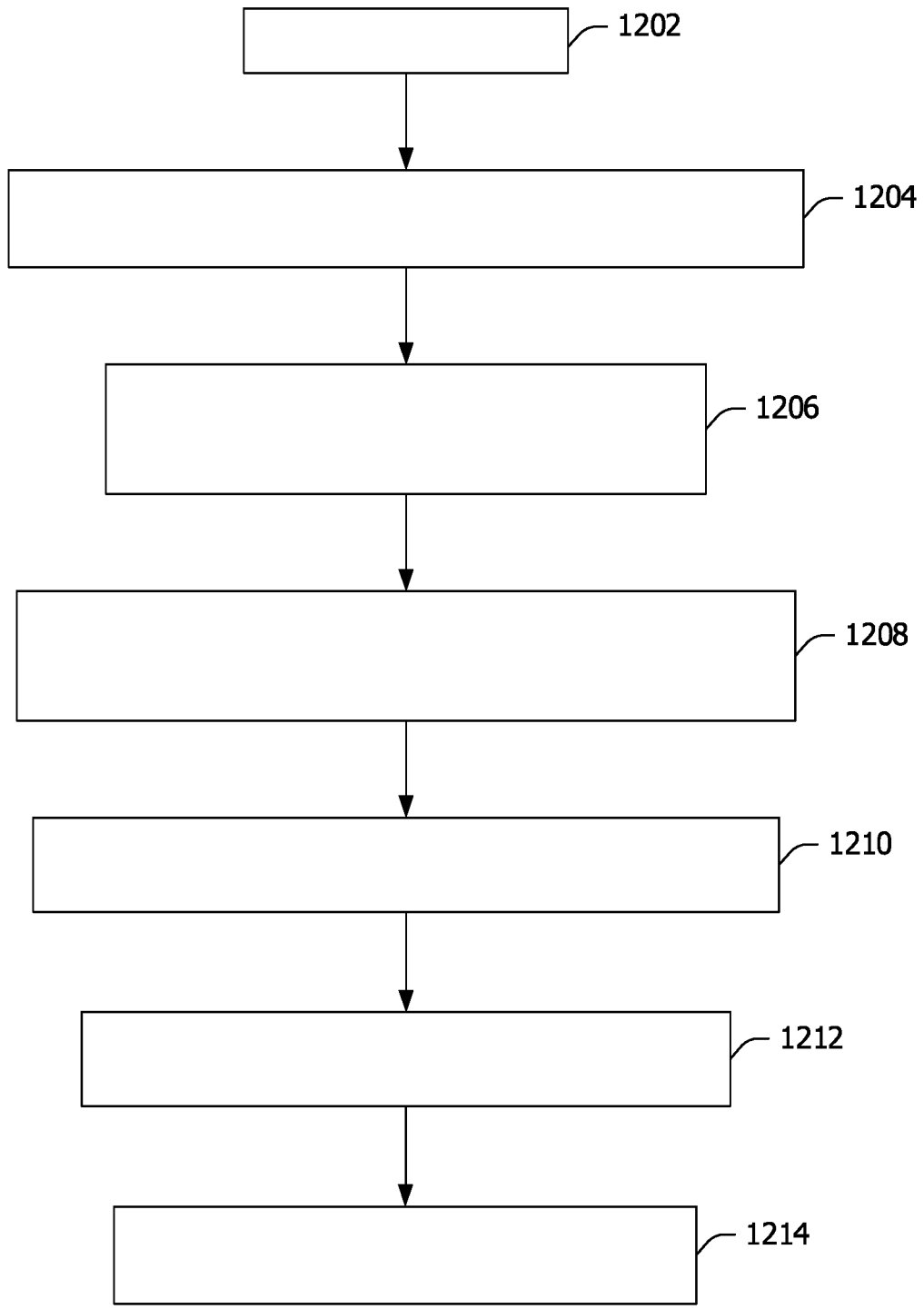
FIG. 12 illustrates an example method, in accordance with an embodiment(s) herein.

FIG. 12 illustrates an example method in accordance with an embodiment(s) herein.

It is to be appreciated that the ordering of the acts in the method is not limiting. As such, other orderings are contemplated herein. In addition, one or more acts may be omitted, and/or one or more additional acts may be included.

At 1202, a 3-D pre-scan is performed, as described herein and/or otherwise.

At 1204, a region/tissue of interest for a 3-D volume scan is identified from a selected scan protocol for the 3-D volume scan, as described herein and/or otherwise.

At 1206, a rendering algorithm is identified based on the selected scan protocol for the 3-D volume scan of the region/tissue of interest, as described herein and/or otherwise.

At 1208, a 2-D pre-scan projection image for planning the 3-D volume scan is created with the 3-D pre-scan data using the identified rendering algorithm, as described herein and/or otherwise.

At 1210, a scan plan for the 3-D volume scan is created using the 2-D pre-scan projection image, as described herein and/or otherwise.

At 1212, a 3-D volume scan of the region/tissue of interest is performed based on the scan plan for the 3-D volume scan, as described herein and/or otherwise.

At 1214, 3-D volumetric image data of the region/tissue of interest is reconstructed from the data acquired during the 3-D volume scan, as described herein and/or otherwise.

The above may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried out by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

The word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An imaging system comprising:
an X-ray radiation source configured to emit radiation that traverses an examination region;
a detector array configured to detect radiation that traverses an examination region and generate a signal indicative thereof, wherein the detected radiation is for a 3-D pre-scan;
a reconstructor configured to reconstruct the signal to generate a 2-D pre-scan projection image; and
a processor and a memory, wherein the processor is configured to execute 3-D volume planning instructions in the memory, which causes the processor to:
display the 2-D pre-scan projection image and a scan plan or bounding box for planning a 3-D volume scan of a region/tissue of interest based on a selected protocol for a 3-D volume scan of a region/tissue of interest being planned; and
receive an input confirming or adjusting the scan plan or bounding box to create a 3-D volume scan plan for the 3-D volume scan of the region/tissue of interest, wherein the 3-D volume scan of the region/tissue of interest is performed based on the 3-D volume scan plan, and wherein the processor is configured to identify the region/tissue of interest based on the selected scan protocol, obtain a rendering algorithm for the identified region/tissue of interest, and render the 2-D pre-scan projection image of the region/tissue of interest based on the obtained rendering algorithm.

2. The system of claim 1, wherein the rendering algorithm is a volume rendering algorithm that projects 3-D volume data into a 2-D plane.

3. The system of claim 1, wherein the rendering algorithm visually enhances the region/tissue of interest in the displayed 2-D pre-scan projection image.

4. The system of claim 1, wherein the rendering algorithm is selected from a group consisting of a maximum intensity projection, a soft tissue/edge interface, a minimum intensity projection, a multiplanar reconstruction, and a curved multiplanar reconstruction.

5. The system of claim 1, wherein the rendering algorithm is selected from a group consisting of a contrast only and a virtual non-contrast image.

6. The system of claim 1, wherein the memory includes a pre-determined mapping between scan protocols and rendering algorithms, and the processor is further configured to select the rendering algorithm from the pre-determined mapping based on the selected scan protocol.

7. The system of claim 1, wherein the processor selects the rendering algorithm based on a user input that identifies the rendering algorithm.

8. The system of claim 1, wherein the processor selects the selected rendering algorithm based on a trained machine learning algorithm.

9. The system of claim 8, wherein the trained machine learning algorithm is trained to map rendering algorithms to scan protocols based at least on one of a rendering algorithm selections of a clinician or a healthcare entity.

10. An imaging method, comprising:
obtaining projection data from a 3-D pre-scan;
reconstructing the projection data to create a 2-D pre-scan projection image;
displaying the 2-D pre-scan projection image and a scan plan or bounding box for planning a 3-D volume scan of a region/tissue of interest based on a selected protocol for a 3-D volume scan of a region/tissue of interest being planned;
identifying the region/tissue of interest based on the selected scan protocol;
obtaining a rendering algorithm for the identified region/tissue of interest;
rendering the 2-D pre-scan projection image of the region/tissue of interest based on the obtained rendering algorithm; and
receiving an input confirming or adjusting the scan plan or bounding box to create a 3-D volume scan plan for the 3-D volume scan of the region/tissue of interest.

11. The method of claim 10, wherein the rendering algorithm visually enhances the region/tissue of interest in the displayed 2-D pre-scan projection image.

12. The method of claim 10, further comprising:
obtaining the rendering algorithm from a pre-determined mapping between scan protocols and rendering algorithms, based on a user input, or selected by a machine learning algorithm.

13. The method of claim 10, further comprising:
performing the 3-D volume scan of the region/tissue of interest based on the 3-D volume scan plan.

14. A non-transitory computer-readable storage medium storing computer executable instructions, which when executed by a processor, cause the processor to:
obtain projection data from a 3-D pre-scan;
reconstruct the projection data to create a 2-D pre-scan projection image;
display the 2-D pre-scan projection image and a scan plan or bounding box for planning a 3-D volume scan of a region/tissue of interest based on a selected protocol for a 3-D volume scan of a region/tissue of interest being planned;
identify the region/tissue of interest based on the selected scan protocol;
obtain a rendering algorithm for the identified region/tissue of interest;
render the 2-D pre-scan projection image of the region/tissue of interest based on the obtained rendering algorithm; and
receive an input confirming or adjusting the scan plan or bounding box to create a 3-D volume scan plan for the 3-D volume scan of the region/tissue of interest.

15. The non-transitory computer-readable storage medium of claim 14, wherein the rendering algorithm visually enhances the region/tissue of interest in the displayed 2-D pre-scan projection image.

16. The non-transitory computer-readable storage medium of claim 14, wherein the computer executable instructions further cause the processor to:
obtain the rendering algorithm from a pre-determined mapping between scan protocols and rendering algorithms, based on a user input, or selected by a machine learning algorithm.

17. The non-transitory computer-readable storage medium of claim 14, wherein the computer executable instructions further cause the processor to:
perform the 3-D volume scan of the region/tissue of interest based on the 3-D volume scan plan.

* * * * *